(12) United States Patent
Silbert

(10) Patent No.: US 10,213,178 B2
(45) Date of Patent: Feb. 26, 2019

(54) CALCULATION OF PERFUSION PARAMETERS IN MEDICAL IMAGING

(71) Applicant: Algotec Systems Ltd., Rochester, NY (US)

(72) Inventor: Ohad Silbert, Rehovot (IL)

(73) Assignee: Algotec Systems Ltd., Ra'anana (IL)

( * ) Notice: Subject to any disclaimer, the term of this patent is extended or adjusted under 35 U.S.C. 154(b) by 11 days.

(21) Appl. No.: 15/706,798

(22) Filed: Sep. 18, 2017

(65) Prior Publication Data
US 2018/0078232 A1 Mar. 22, 2018

Related U.S. Application Data

(60) Provisional application No. 62/397,993, filed on Sep. 22, 2016.

(51) Int. Cl.
*G06K 9/00* (2006.01)
*A61B 6/00* (2006.01)
(Continued)

(52) U.S. Cl.
CPC .......... *A61B 6/5258* (2013.01); *A61B 5/0042* (2013.01); *A61B 5/0263* (2013.01);
(Continued)

(58) Field of Classification Search
CPC ....... A61B 6/5258; A61B 6/481; A61B 6/501; A61B 6/032; A61B 6/507; A61B 6/5217;
(Continued)

(56) References Cited

U.S. PATENT DOCUMENTS

| 7,567,832 B2 * | 7/2009 | Schmainda | A61K 49/06 324/306 |
| 8,718,747 B2 * | 5/2014 | Bjornerud | A61B 5/055 382/128 |

(Continued)

OTHER PUBLICATIONS

Anna K. Heye et al., "Assessment of blood-brain barrier disruption using dynamic contrast-enhanced MRI. A systematic review," NeuroImage: Clinical, 6, 2014, pp. 262-274.

(Continued)

*Primary Examiner* — John B Strege

(57) ABSTRACT

A method of determining a residue function in brain tissue, from medical images acquired after introducing contrast agent into the blood, correcting for contrast agent leakage into the tissue, comprising: a) providing time signals indicating contrast agent concentration for leaking voxels, a time signal indicating average contrast agent concentration for non-leaking voxels, and an artery input function, all derived from the images; b) fitting the leaking voxel signals to a model time signal with a free parameter for leakage rate, the model assuming that the concentration of contrast agent perfusing through a leaking voxel has a same shape as a function of time as the average contrast agent concentration for non-leaking voxels; c) using the best fit leakage rate parameter to make a correction for leakage to the leaking voxel signals; and d) deconvolving the corrected signals from the artery input function, to find the residue function.

17 Claims, 10 Drawing Sheets

(51) Int. Cl.
  *A61B 5/026* (2006.01)
  *A61B 5/00* (2006.01)
  *G01R 33/56* (2006.01)
  *G01R 33/563* (2006.01)
  *G06T 7/11* (2017.01)
  *G06T 7/00* (2017.01)
  *A61B 6/03* (2006.01)
  *A61B 5/0295* (2006.01)
  *A61B 5/055* (2006.01)

(52) U.S. Cl.
  CPC .............. *A61B 6/032* (2013.01); *A61B 6/481* (2013.01); *A61B 6/501* (2013.01); *A61B 6/507* (2013.01); *A61B 6/5217* (2013.01); *G01R 33/5601* (2013.01); *G01R 33/56366* (2013.01); *G06T 7/0016* (2013.01); *G06T 7/11* (2017.01); *A61B 5/0295* (2013.01); *A61B 5/055* (2013.01); *A61B 5/7203* (2013.01); *A61B 5/7278* (2013.01); *A61B 2576/026* (2013.01); *G06T 2207/10081* (2013.01); *G06T 2207/10096* (2013.01); *G06T 2207/30016* (2013.01); *G06T 2207/30104* (2013.01)

(58) Field of Classification Search
  CPC ..... A61B 5/0042; A61B 5/055; A61B 5/0295; A61B 5/7203; A61B 5/7278; A61B 2576/026; G06T 7/0016; G06T 7/11; G06T 2207/10096; G06T 2207/30016; G06T 2207/30104; G06T 2207/10081; G01R 33/56366; G01R 33/5601
  See application file for complete search history.

(56) References Cited

U.S. PATENT DOCUMENTS

| | | | | |
|---|---|---|---|---|
| 9,649,041 | B2* | 5/2017 | Ohyu | A61B 5/0263 |
| 2006/0083687 | A1* | 4/2006 | Yang | A61B 5/0263 424/9.3 |
| 2007/0167731 | A1* | 7/2007 | Taxt | G01R 33/5601 600/410 |
| 2010/0296714 | A1* | 11/2010 | Schmainda | A61B 5/0263 382/131 |
| 2011/0257519 | A1* | 10/2011 | Bj?rnerud | A61B 5/055 600/431 |
| 2012/0141005 | A1* | 6/2012 | Djeridane | A61B 5/02028 382/131 |
| 2013/0039553 | A1* | 2/2013 | Kjolby | A61B 5/026 382/128 |
| 2015/0208930 | A1* | 7/2015 | Gall | A61B 5/0263 600/420 |
| 2016/0166159 | A1* | 6/2016 | Yang | G06T 7/11 600/419 |
| 2016/0228085 | A1* | 8/2016 | Mouridsen | A61B 6/5217 |
| 2016/0245889 | A1* | 8/2016 | Djeridane | A61B 6/486 |

OTHER PUBLICATIONS

R. M. Weisskoff et al., "Simultaneous Blood Volume and Permeability Mapping Using a Single Gd-Based Contrast Injection," Proceedings of the Society of Magnetic Resonance Imaging, 1994 (Suppl. 1), p. 279.

Atle Bjørnerud et al., "$T_1$- and $T_2$*-dominant extravasation correction in DSC-MRI: Part I—theoretical considerations and implications for assessment of tumor hemodynamic properties," Journal of Cerebral Blood Flow & Metabolism, 2011, 31, pp. 2041-2053.

C. C. Quarles et al., "Improving the Reliability of Obtaining Tumor Hemodynamic Parameters in the Presence of Contrast Agent Extravasation," Magnetic Resonance in Medicine, 53, 2005, pp. 1307-1316.

Ona Wu et al., "Tracer Arrival Timing-Insensitive Technique for Estimating Flow in MR Perfusion-Weighted Imaging Using Singular Value Decomposition With a Block-Circulant Deconvolution Matrix," Magnetic Resonance in Medicine, 50, 2003, pp. 164-174.

Andreas Fieselmann et al., "Deconvolution-Based CT and MR Brain Perfusion Measurement: Theoretical Model Revisited and Practical Implementation Details," International Journal of Biomedical Imaging, vol. 2011, Article ID 467563, 20 pages.

Paul Meier et al., "On the Theory of the Indicator-Dilution Method for Measurement of Blood Flow and Volume," Journal of Applied Physiology, vol. 6, No. 12, 1954, pp. 731-744.

Antoinette A. Chan et al., "Simplified Gamma-Variate Fitting of Perfusion Curves," Biomedical Imaging: Nano to Macro, vol. 2, 2004, IEEE International Symposium, pp. 1067-1070.

Henrik B. W. Larsson et al., "Measurement of Brain Perfusion, Blood Volume, and Blood-Brain Barrier Permeability, Using Dynamic Contrast-Enhanced $T_1$-Weighted MRI at 3 Tesla," Magnetic Resonance in Medicine, 62, 2009, pp. 1270-1281.

J. L. Boxerman et al., "Relative Cerebral Blood Volume Maps Corrected for Contrast Agent Extravasation Significantly Correlate with Glioma Tumor Grade, Whereas Uncorrected Maps Do Not," Am J. Neuroradiol, 27, 2006, pp. 859-867.

Wikipedia article on "Wiener Deconvolution," <https://en.wikipedia.org/w/index.php?title=Wiener?deconvolution&oldid=700573288>, printed on Sep. 15, 2017, 3 pages.

G. Larry Bretthorst, "Bayesian Interpolation and Deconvolution," Technical Report CR-RD-AS-92-4, Prepared for the Advanced Sensor Directorate Research Development, and Engineering Center Contract No. DAAL03-86-D-0001, 1992, 46 pages, <http://citeseerx.ist.psu.edu/viewdoc/summary? Doi=10.1.1.46.3051>.

Wikipedia article on "Well-posed problem," <https://en.wikipedia.org/w/index.php?title=Well-posed_problem&oldid=690413559>, printed on Sep. 15, 2017, 1 page.

Wikipedia article on "Condition number," <https://en.wikipedia.org/w/index.php?title=Condition_number&oldid=718497277, printed on Sep. 15, 2017, 4 pages.

Wikipedia article on "Tikhonov regularization," https://en.wikipedia.org/e/index.php?title=Tikhonov_regularization&oldid=720904657, printed on Sep. 15, 2017, 4 pages.

P. C. Hansen, "The L-curve and its use in the numerical treatment of inverse problems," Computationsl Inverse Problems in Electrocardiology, No. 5, 2001, Advances in Computational Bioengineering, 24 pages.

Thomas A. Bronikowski et al., "Model-Free Deconvultion Techniques for Estimating Vascular Transport Functions," Int. J. Bio-Medical Computing, 14, 1983, pp. 411-429.

G. T. Gobbel et al., "A deconvolution method for evaluating indicator-dilution curves," Phys. Med. Biol., 39, 1994, pp. 1833-1854.

Wikipedia article on "Moore-Penrose pseudoinverse," Sep. 2018 https://en.wikipedia.org/w/index.php?title=Moore%E2%80%93Penrose_pseudoinverse&oldid=719834705 8 pages.

Thomas A. Bronikowski et al., "Model-Free Deconvolution Techniques for Estimating Vascular Transport Functions," Int. J. Bio-Medical Computing, 14, 1983, pp. 411-429.

\* cited by examiner

CALCULATION OF PERFUSION PARAMETERS IN MEDICAL IMAGING

CROSS REFERENCE TO RELATED APPLICATIONS

This application claims the benefit of U.S. Provisional 62/397,993, provisionally filed on Sep. 22, 2016, entitled "CALCULATION OF PERFUSION PARAMETERS IN DSC MRI IMAGING," in the name of Ohad SILBERT, incorporated herein by reference as if fully set forth in their entirety.

FIELD AND BACKGROUND OF THE INVENTION

The present invention, in some embodiments thereof, relates to a method of finding perfusion parameters from medical images and, more particularly, but not exclusively, to a method of finding cerebral perfusion parameters from MRI or CT images of the brain.

Various medical imaging modalities can be useful for measuring rates of perfusion of body tissue as a function of position in the tissue, to detect the precise location and extent of deficiencies in perfusion. Such methods are important for evaluating brain tumors, which are often associated with deficiencies in perfusion, and with leakage of blood or components of blood out of the capillaries. They are also important for detecting and localizing strokes by imaging brain tissue, since effective treatment of strokes can depend critically on rapid diagnosis. These imaging modalities can be used to measure perfusion parameters by introducing an appropriate contrast agent into the bloodstream of a subject, and creating images showing the subsequent concentration of the contrast agent as a function of time and position in the brain. Image processing methods, performed with a computer, can then use the images to find the values of various hemodynamic parameters as a function of position, for example cerebral blood volume (CBV), cerebral blood flow (CBF), mean transit time (MTT), time to peak contrast agent concentration (TTP), and the peak time of the residue function (TMAX). A localized deficit in CBF, for example, can indicate the presence and location of an ischemic stroke. Dynamic susceptibility contrast (DSC) magnetic resonance imaging (MRI) is a commonly used technique for measuring hemodynamic parameters in the brain, using a paramagnetic contrast agent, such as a gadolinium-based contrast agent, for example Gd-DPTA. Such contrast agents primarily affect the effective transverse relaxation time $T_2^*$ when they are in the bloodstream, and DSC-MRI uses pulse sequences that are weighted to show differences in $T_2^*$, or equivalently, changes in the effective transverse relaxation rate $R_2^*$, defined as $1/T_2^*$. The most straightforward image processing techniques for obtaining hemodynamic parameters from DSC-MRI images assume that no contrast agent leaks out of the bloodstream into the extravascular extracellular space (EES) of the tissue. That assumption can be checked by seeing whether a significant concentration of contrast agent remains in the tissue about 60 to 90 seconds after the contrast agent is introduced into the bloodstream, since by that time, the contrast agent in the blood has spread out enough to have only a very low concentration.

Other imaging and image processing techniques, also using contrast agent, can be used to detect and measure leakage of blood vessels into the EES, particularly in the brain where such leakage can indicate a breakdown in the blood-brain barrier. For example, paramagnetic contrast agents such as gadolinium-based agents tend to primarily affect $T_1$ when they are located in the EES, and for this reason dynamic contrast enhanced (DCE) MRI, weighted toward differences in $T_1$, is often used to detect leakage from blood vessels in the brain, for example due to brain lesions.

In some medical conditions, such as certain brain tumors, both leakage, and abnormalities in perfusion and other hemodynamic parameters, may be present at the same location, and various models have been proposed, and used to motivate image processing techniques for accurately determining hemodynamic parameters even in the presence of leakage. Some of these models are described in a review paper by Anna K. Heye, Ross D. Culling, Maria del C. Valdés Hernández, Michael J. Thrippleton, and Joanna M. Wardlaw, "Assessment of blood-brain barrier disruption using dynamic contrast-enhanced mri. a systematic review," NeuroImage: Clinical, 6:262-274, 2014. ISSN2213-1582. doi: http://dx.doi.org/10.1016/j.nicl.2014.09. 002.

R. M. Weisskoff, J. L. Boxerman, A. G. Sorensen, S. F. Kulke, T. A. Campbell, and B. R. Rosen, "Simultaneous blood volume and permeability mapping using a single Gd-based contrast injection," Proceedings of the Society of Magnetic Resonance Imaging 1994 (Suppl. 1), p. 279, describes a robust strategy for correcting T1 enhancement in Gd-based regional cerebral blood volume (rCBV) maps, in regions where T1 effects are significant, such as tissue with blood-brain barrier breakdown, to produce both corrected rCBV maps as well as permeability maps in clinical studies.

Atle Bjornerud, A Gregory Sorensen, Kim Mouridsen, and Kyrre E Emblem, "$T_1$- and $T_2^*$-dominant extravasation correction in DSC-MRI: Part I—theoretical considerations and implications for assessment of tumor hemodynamic properties," Journal of Cerebral Blood Flow & Metabolism, 31(10):2041-2053, 2011, describes a novel contrast agent extravasation-correction method based on analysis of the tissue residue function for assessment of multiple hemodynamic parameters. The method enables semiquantitative determination of the transfer constant, while being insensitive to variations in tissue mean transit time (MTT).

C. C. Quarles, B. D. Ward, and K. M. Schmainda, "Improving the reliability of obtaining tumor hemodynamic parameters in the presence of contrast agent extravasation." Magnetic Resonance in Medicine, 53 (6):1307-1316, 2005, describes a new approach to improve the reliability of dynamic susceptibility contrast MRI for the evaluation of brain tumor hemodynamics in the presence of contrast agent extravasation. The model-based technique simultaneously estimates the voxel-wise tumor residue function and the temporal extravasation $T_1$ changes following contrast agent leakage. With these estimates the model corrects the measured MRI signal, which is then used to calculate tumor hemodynamic parameters. Quarles et al point out some disadvantages of using the method of Weisskoff et al, cited above, and state that, in Weiskoff et al, "it is assumed that a leaky tumor $\Delta R2^*(t)$ can be modeled as a scaled version of $\Delta R2^*(t)$ from healthy tissue. Given that tumor hemodynamics are extremely heterogeneous across and within the same tumor, this is probably not a good assumption. Thus we hypothesize that an improved estimate must allow for this heterogeneity."

Additional background art includes Ona Wu, Leif Østergaard, Robert M. Weisskoff, Thomas Benner, Bruce R. Rosen, and A. Gregory Sorensen, "Tracer arrival timing insensitive technique for estimating flow in mr perfusion-weighted imaging using singular value decomposition with a block-circulant deconvolution matrix," Magnetic Resonance in Medicine, 50(1):164-174, 2003; Andreas Fieselmann, Markus Kowarschik, Arundhuti Ganguly, Joachim Hornegger, and Rebecca Fahrig, "Deconvolution-based ct and mr brain perfusion measurement: Theoretical model revisited and practical implementation details," International Journal of Biomedical Imaging, 2011: 20, 2011; Paul Meier and Kenneth L. Zierler, "On the theory of the indicator dilution method for measurement of blood flow and volume," Journal of Applied Physiology, 6(12):731-744, 1954; A. A. Chan and S. J. Nelson, "Simplified gamma-variate fitting of perfusion curves," Biomedical Imaging: Nano to Macro, 2004, IEEE International Symposium on, pages 1067-1070 Vol. 2, April 2004; Henrik B. W. Larsson, Frédéric Courivaud, Egill Rostrup, and Adam E. Hansen, "Measurement of brain perfusion, blood volume, and blood brain barrier permeability, using dynamic contrast-enhanced t1 weighted mri at 3 tesla," Magnetic Resonance in Medicine, 62(5): 1270-1281, 2009; J. L. Boxerman, K. M. Schmainda, and R. M. Weisskoff, "Relative cerebral blood volume maps corrected for contrast agent extravasation significantly correlate with glioma tumor grade, whereas uncorrected maps do not,". American Journal of Neuroradiology, 27(4): 859-867, 2006; and published U. S. patent application 2011/0257519 to Bjornerud et al.

SUMMARY OF THE INVENTION

An aspect of an embodiment of the invention concerns a method for finding corrected hemodynamic parameters in tissue in which some voxels exhibit leakage of contrast agent from blood vessels into the extravascular extracellular space (EES), using data from medical images acquired after introducing the contrast agent into the blood. The method first assumes that contrast agent concentration in the capillaries has, to first order, the same time dependence in leaking voxels as an average for non-leaking voxels, and that the contrast agent in the EES of each leaking voxel builds up at a rate proportional to the contrast agent concentration in the capillaries, and the method uses the measured signal in each of at least some of the leaking voxels in the medical images to find a best fit to a leakage rate parameter for that voxel. The EES estimated contribution to the signal is then removed to find a corrected signal that gives a corrected contrast agent concentration, only in the capillaries, in each of those leaking voxels, and the corrected contrast agent concentration is deconvolved from an arterial input function of contrast agent concentration to find a corrected residue function and hemodynamic parameters in those voxels.

There is thus provided, in accordance with an exemplary embodiment of the invention, a method of determining a residue function for perfusion at one or more locations in a subject's brain tissue, from a series of medical images of the tissue acquired using a medical imaging modality at successive times after introducing a contrast agent into the subject's blood stream, the method correcting for a leakage of the contrast agent out of the blood stream into extravascular extracellular space (EES) of the tissue, the method comprising:

a) providing to a data processor a signal indicating contrast agent concentration as a function of time for one or more voxels of the tissue that exhibit the leakage at a significant level, a signal indicating an average or typical contrast agent concentration as a function of time for non-leaking voxels of the tissue, and an artery input function indicating a concentration of the contrast agent as a function of time in the arteries feeding into the tissue, the signals and artery input function being derived from the images;

b) fitting the signal for the voxels exhibiting leakage to an expected value for the signal as a function of time, using the data processor, according to a model with free parameters including at least a parameter depending on leakage rate, the model assuming that the concentration of contrast agent in the blood perfusing through a voxel has a same shape as a function of time as the average or typical contrast agent concentration for the non-leaking voxels;

c) using the model and best fit leakage rate parameter to find and make an expected correction for leakage, to the signal for contrast agent concentration as a function of time, for the voxels exhibiting leakage, using the data processor; and d) deconvolving the corrected signal for the voxels exhibiting leakage from the artery input function, to find the residue function for those voxels, using the data processor.

Optionally, the imaging modality comprises computerized tomography (CT).

Alternatively, the imaging modality comprises magnetic resonance imaging (MRI), and the contrast agent comprises a paramagnetic contrast agent.

Optionally, the MRI comprises dynamic susceptibility contrast (DSC) MRI.

Optionally, providing the arterial input function comprises: a) segmenting artery voxels in the medical images; b) determining a concentration of the contrast agent in at least a portion of the artery voxels as a function of time; and c) setting the arterial input function at the time when each of the medical images was acquired to a value based on a distribution of the concentration of contrast agent determined for the artery voxels in that medical image.

Optionally, deconvolving the corrected signal comprises finding an inverse or pseudo-inverse of a matrix whose elements have values based on values of the corrected signal at a plurality of different times.

Optionally, finding the inverse or pseudo-inverse of the matrix comprises regularizing the matrix.

Optionally, providing a signal indicating an average or typical contrast agent concentration as a function of time for non-leaking voxels of the tissue comprises: a) identifying non-leaking voxels of the tissue in the images; and b) deriving the signal for each image acquisition time from image intensities for the identified non-leaking voxels in the image acquired at that time.

Optionally, identifying non-leaking voxels of the tissue comprises: a) segmenting and excluding voxels of blood vessels in the images; b) selecting a late time range, long enough after the contrast agent is introduced so that a concentration of contrast agent in non-leaking voxels averaged over the late time range is expected to be at least 10 times lower than a peak concentration in that voxel; c) identifying a range of possible signal amplitudes in the images that are expected for non-leaking voxels, but not for significantly leaking voxels, averaged over the late time range; and d) identifying voxels as non-leaking voxels if their signal amplitudes, averaged over the late time range, falls within the range expected for non-leaking voxels.

Optionally, providing a signal indicating contrast agent concentration for one or more voxels of the tissue that exhibit the leakage at a significant level comprises: a) identifying the one or more voxels that exhibit the leakage at a significant level; and b) deriving the signal for each image acquisition time, for each of the one or more voxels, from an image intensity for that voxel in the image acquired at that time.

Optionally, identifying voxels that exhibit leakage at a significant level comprises: a) segmenting and excluding voxels of blood vessels in the images; b) selecting a late time range, long enough after the contrast agent is introduced so that a concentration of contrast agent in non-leaking voxels averaged over the late time range is expected to be at least 10 times lower than a peak concentration in that voxel; c) identifying a range of possible signal amplitudes in the images that are expected for voxels that exhibit leakage at a significant level, but not for non-leaking voxels, averaged over the late time range; and d) identifying voxels as exhibiting leakage at a significant level if their signal amplitude, averaged over the late time range, falls within the range expected for voxels that exhibit leakage at a significant level.

In an embodiment of the invention, the model assumes that in each voxel, a permeability of capillaries to contrast agent does not change substantially over the times when the medical images are acquired, and that during those times, a concentration of contrast agent in the EES of that voxel increases at a rate that is proportional to the permeability times a concentration of the contrast agent in the capillaries of that voxel, neglecting any flow of contrast agent from the EES back into the capillaries.

Alternatively, the model assumes that in each voxel, a permeability of capillaries to contrast agent does not change substantially over the times when the medical images are acquired, and that during those times, a concentration of contrast agent in the EES of that voxel increases at a rate that is proportional to the permeability times a concentration of the contrast agent in the capillaries of that voxel minus a concentration of the contrast agent in the EES of that voxel.

Optionally, the method also comprises using the residue functions for those voxels to find one or more hemodynamic parameters for those voxels.

Optionally, the hemodynamic parameters comprise one or more of a cerebral blood volume (CBV), a cerebral blood flow (CBF), a mean transit time (MTT), and a time of maximum value of the residue function (TMAX).

Optionally, the free parameters of the model also include one or more other parameters in addition to the parameter that depends on leakage rate.

Optionally, the one or more other parameters comprise a parameter that depends on blood volume.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1:
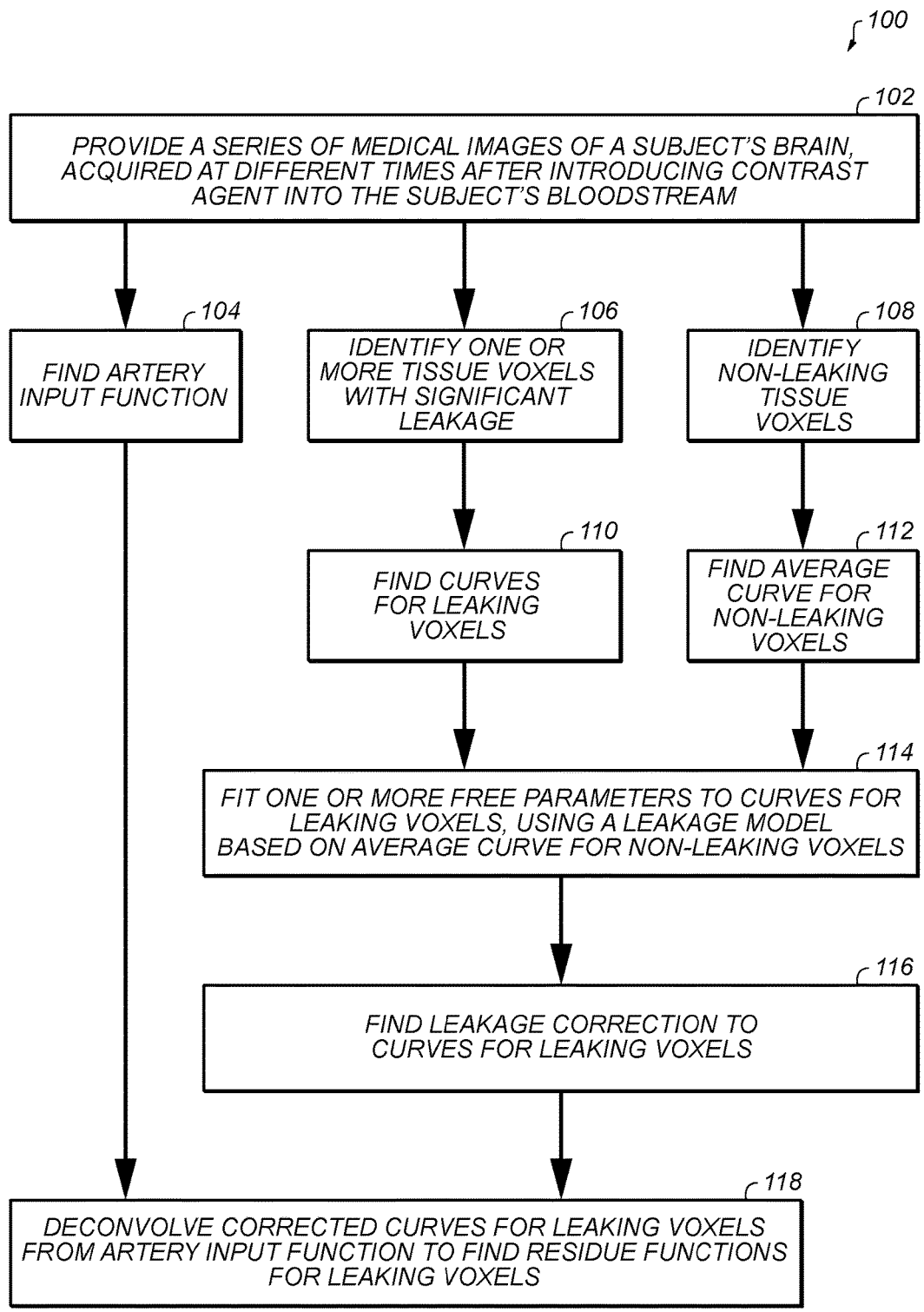
FIG. 1 is a flowchart showing a method of finding a residue function corrected for leakage of contrast agent, according to an exemplary embodiment of the invention.

The present invention, in some embodiments thereof, relates to a method of finding perfusion parameters from medical images and, more particularly, but not exclusively, to a method of finding cerebral perfusion parameters from MRI or CT images of the brain.

An aspect of some embodiments of the invention concerns a method of finding a perfusion residue function, at different positions in brain tissue of a subject, using data derived from a series of medical images of the tissue acquired at a plurality of successive times after introducing a contrast agent into the subject's bloodstream, and correcting the measured concentration of contrast agent in the capillaries at each voxel for leakage of the contrast agent into the extravascular extracellular space (EES). The method first obtains a signal as a function of time for concentration of contrast agent in the capillaries averaged over voxels that do not exhibit leakage, and initially assumes that the same function applies to the concentration of contrast agent in the capillaries of leaking voxels, in order to find a correction for leakage for those voxels. The corrected contrast agent concentration in the capillaries as a function of time is then used to find a corrected residue function for the leaking voxels, for example by deconvolving the corrected contrast agent concentration from an artery input function. Optionally, the corrected residue function is then used to find hemodynamic parameters for the leaking voxels, for example cerebral blood flow (CBF), cerebral blood volume (CBV), mean transit time (MTT), and TMAX (time of peak value of the residue function). Optionally, the corrected contrast agent concentration is also used to find other perfusion parameters, such as time to peak of the contrast agent concentration (TTP), for the leaking voxels.

The method is expected to work best for voxels which either have small leakage, or have a residue function close to that of non-leaking voxels, or both, though it might produce satisfactory results even if the leakage is fairly large and the residue function is not so close to that for non-leaking voxels. Unlike the methods described in some prior art, such as the method of Bjornerud, or the method of Quarles, cited above, this method does not assume that that at the short times over which the residue function is significantly greater than zero, leakage is negligible, and at the longer times over which significant leakage occurs, the residue function is negligibly small.

Optionally, the medical imaging modality is MRI, optionally dynamic susceptibility contrast (DSC) MRI, weighted to emphasize differences in $T_2^*$, which is typically used for evaluating hemodynamic parameters in the brain, using a paramagnetic contrast agent, such as a gadolinium-based contrast agent. Alternatively, MRI imaging with a different weighting is used, or a different imaging modality, such as computerized tomography (CT), is used, with an appropriate contrast agent for the imaging modality used. When DSC-MRI imaging is used, the contrast agent that leaks into the EES generally produces an effect on the signal of the opposite sign of the contrast agent in the capillaries, because contrast agent in the EES affects the MRI signal predominantly through its reduction in $T_1$, while contrast agent in the capillaries affects the MRI signal predominantly through its reduction in $T_2^*$. The signal at late times, after the contrast agent has largely dissipated in the capillaries but remains in the EES, is often negative in this case, i.e. opposite in sign to the signal when the contrast agent concentration is at its peak in the capillaries. Correcting the signal for leakage in this case involves adding a correction term of the same sign as the uncorrected signal when the contrast agent concentration is at its peak. When CT imaging is used, the contrast agent that leaks into the EES generally produces an effect on the signal of the same sign as the contrast agent in the capillaries. Correcting the signal for leakage in this case involves subtracting a correction term of the same sign as the uncorrected signal when the contrast agent concentration is at its peak.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Referring now to the drawings, FIG. 1 shows a flowchart 100 for a method of finding a residue function for different locations in a subject's brain, using medical images of the subject's brain tissue acquired after introducing a contrast agent into the subject's bloodstream, including corrections for leakage of the contrast agent in some voxels, according to an exemplary embodiment of the invention. The residue function can be used to find hemodynamic parameters of the brain. The drawings refer to finding a residue function in brain tissue using DSC-MRI images of the brain, but the method could also be adapted to other imaging modalities, such as CT.

At 102, a series of medical images of the subject, that include at least part of the brain, are provided, the images having been acquired at a series of different times after the contrast agent was introduced into the subject's bloodstream. The acquisition times include several different times during the period, typically about 30 seconds long, when the contrast agent first reaches the arteries of the brain and passes through the capillaries of the brain tissue, and the acquisition times are at close enough intervals, for example every 1 to 3 seconds, to provide good time resolution of that process. Images are optionally also acquired for a period before that, for example starting when the contrast agent is first introduced into the bloodstream, to provide a baseline signal before there is any contrast agent in the brain, and for a period after that, for example for about a minute after the contrast agent first reaches the brain, until the contrast agent remaining in the bloodstream has spread out enough to have a much smaller concentration than at its peak value, but contrast agent that has leaked out of the capillaries into the extravascular extracellular space (EES) in the brain tissue to a significant extent is still detectable in the images, thus providing a measure of leakage.

The images provided at 102 are optionally registered to each other, so that, for any given voxel in one image, it is possible to identify the corresponding voxels in the other images acquired at different times. This makes it possible to find the value of the imaging signal, in this case the MRI signal, as a function of time for each location in the brain tissue that was imaged. As used herein, "identifying a voxel" in the images means identifying a series of corresponding voxels in the series of images acquired at different times, and often the behavior of the imaging signal as a function of time is used to identify voxels with certain characteristics, for example voxels with leakage, or non-leaking voxels.

If the subject has not moved very much between the acquisition time of any two images, for example less than the width of a voxel, then the raw images are already considered to be registered, and optionally no specific registration procedure is performed on the images. Optionally, the images as provided are smoothed over a distance scale comparable to a voxel width, for example 1 mm, so that very small motions of the subject, for example of half a voxel width, between images acquired at different times, do not result in large differences in signal amplitude in corresponding voxels between one image and the other, due to this motion, and any changes in signal amplitude in corresponding voxels in different images are due almost entirely to real changes in time at a given location in the subject's body. Optionally, for example if the subject is known or suspected to have possibly moved a significant distance between image acquisition times, then a registration procedure is performed on the images before they are provided.

The images as provided are optionally segmented, distinguishing brain voxels from any voxels located outside the brain, and within the brain, distinguishing voxels corresponding to larger blood vessels, those greater in diameter than the width of a voxel, from tissue voxels that only contain small blood vessels and capillaries, too small to resolve in the image. As used herein, "tissue voxels" or "voxels of the tissue" excludes voxels whose volume is entirely or largely made up of larger blood vessels, those with diameter greater than the width of a voxel.

Alternatively, the images when they are provided are not registered to each other, and/or they are not segmented, and any registration, smoothing, and/or segmentation is done after they are received, optionally by a data processor that is also performing the method of flowchart 100. The registration may be done by any known method of registering a time series of medical images of the same tissue. For example, the difference in location of the center of mass of two images is used to find a translation between them, and principle component analysis is used to find a rigid rotation between the two images, to bring them into alignment, so that corresponding voxels in the two images will correspond to the same location in the subject's body. The segmentation may be done by any known method of segmenting brain tissue, at least distinguishing the brain from parts of the image that are external to the brain, and distinguishing blood vessels from other brain tissue. For example, a threshold in image intensity, and/or a threshold of a quantity derived from a histogram of image intensities in a small region, optionally in images acquired before contrast agent reaches the brain, is optionally used to distinguish voxels that are part of the brain from voxels that are outside the brain, optionally also to distinguish brain tissue voxels from blood vessel voxels within the brain. Optionally, the image intensity in each voxel believed to be a brain voxel is examined as a function of time, to see if it shows an increase and then a decrease in contrast agent concentration at approximately the expected times, and if the voxel does not show such an increase and decrease in contrast agent concentration, then it is considered not to be a brain voxel. Optionally, morphological operations, such as filling holes, are performed after these initial segmentation procedures, for example assigning voxels to the brain if they are completely surrounded by brain voxels, even if initially, due for example to their image intensity, they were considered to be outside the brain. In some embodiments of the invention, the image voxels are never segmented into brain voxels and non-brain voxels, and the method of flowchart 100 is performed on all voxels in the image. Any voxels that are actually outside the brain will, in that case, show a contrast agent concentration that is zero, or at the noise level, throughout the period when images were acquired.

Once the images have been registered, the MRI signal can be found as a function of time at the location of each voxel, and can be used to find a measure of contrast agent concentration at each voxel as a function of time. The same thing can be done with a CT signal, or a signal from any other imaging modality. In DSC-MRI, the signal intensity as a function of time is given by:

$$S(t) = PD(1 - e^{-TR \cdot R_1}) e^{-TE \cdot R^*_2(t)}$$

where PD is the proton density, TR is the repetition time, TE is the echo-time, $R_1$ is the spin-lattice relaxation rate (equal to $1/T_1$) and $R^*_2$ is the spin-spin relaxation rate (equal to $1/T_2^*$). When contrast agent reaches the tissue being imaged, the spin-spin relaxation rate changes proportionally to the contrast material concentration C(t):

$$R^*_2 \rightarrow R^*_2 + \Delta R^*_2(t) \text{ where } \Delta R^*_2(t) \text{ is proportional to } C(t).$$

In order to find the concentration of contrast agent, the logarithm of the intensity of the MRI signal S(t) is computed:

$$\Delta R^*_2(t) = -\frac{1}{TE} \log \frac{S(t)}{S(0)}$$

where it is assumed that the concentration is 0 at t=0, before any contrast agent has reached the brain. In the case of DSC-MRI imaging, it is usual to define a signal $\Delta R_2^*(t)$ in this way, ignoring the effect of any changes in $T_1$ on the signal. Then, if there has not been any significant leakage of contrast agent at that voxel, $\Delta R_2^*(t)$ will be positive and proportional to the concentration of contrast agent in the capillaries. The signal $\Delta R_2^*(t)$ is referred to herein as a "signal indicating a concentration of contrast agent," even though, when enough contrast agent has leaked into the EES, this signal is no longer an accurate measure of contrast agent concentration, due to the effect of contrast agent in the EES on $T_1$, which has the opposite effect on the signal amplitude S(t) as contrast agent in the capillaries. In particular, at later times, after contrast agent has largely dissipated from the capillaries but remains in the EES of significantly leaking voxels, $\Delta R_2^*(t)$ will generally become negative and remain negative. A goal of the method of flowchart 100 is to correct this observed signal $\Delta R_2^*(t)$ to produce a corrected signal $\Delta R_2^*(t)$ that really does indicate the concentration of contrast agent in the capillaries of the voxel, even in the presence of leakage.

For other imaging modalities, a different signal is optionally defined that is expected to be at least approximately proportional to the concentration of whatever contrast agent is used for that imaging modality. For CT, for example, the signal may be the difference in the image intensity, in Hounsfield units, between time t and an average during a baseline period before the contrast agent has reached the brain. In this case, though, contrast agent in the EES will generally have the same effect on the signal as contrast agent in the capillaries.

At 104, an artery input function is found for the series of images, for example by using voxels identified as artery voxels in the images to determine $\Delta R_2^*(t)$ in the artery voxels. For example the artery input function at a time t is found from an average of $\Delta R_2^*(t)$ over the artery voxels, such as a mean value, a median value, or a modal value, taken over all identified artery voxels, or over a portion of them. The inventors have found that using a median value gives good results, using only a portion of the artery voxels that have the highest peak values of $\Delta R_2^*(t)$. Optionally, only a portion of artery voxels with their peak values of $\Delta R_2^*(t)$ earliest in time, or with peak values both high and early in time, are used. Artery voxels with lower peak $\Delta R_2^*(t)$, and/or with peak $\Delta R_2^*(t)$ later in time, may include some tissue other than the blood inside arteries as part of their volume, and they are optionally not included in the average. The artery voxels that are included, with their volume comprising only blood, are from larger arteries, with diameter greater than the width of a voxel. Optionally, artery voxels in the images are distinguished from vein voxels, among large blood vessel voxels, because their peak concentration of contrast agent occurs earlier, for example about 2 seconds earlier, due to the time needed for the greatest concentration of contrast agent to perfuse through the capillaries to reach the veins. If this method of distinguishing artery and vein voxels is used, then the artery and vein voxels need not already be segmented from each other, in the images provided at 102. Alternatively, some other method of distinguishing artery and vein voxels, based for example on the appearance of the blood vessel walls, is used. It should be noted that finding the peak $\Delta R_2^*(t)$ in a voxel can also be used to segment voxels of larger blood vessels from voxels of other brain tissue, since the peak $\Delta R_2^*(t)$ will generally be higher in voxels of larger blood vessels, which are 100% blood, than in other tissue voxels, which have a volume fraction of blood equal to the cerebral blood volume (CBV) for that voxel, less than 100%.

Optionally, the artery input function is assumed to be the same for all voxels in the image. Alternatively, differences in timing of the artery input function in different regions of the brain are taken into account.

At 106, tissue voxels in the brain with significant leakage are identified, and at 108, non-leaking tissue voxels in the brain are identified. As used herein, a voxel with "significant" or "substantial" leakage means a voxel with a level of leakage that can be clearly detected, and used to distinguish the voxel from non-leaking voxels, in the images. For example, in the case of DSC-MRI imaging, this refers to voxels with a great enough level of leakage so that their $\Delta R_2^*(t)$ signal at late times is clearly negative, when noise is removed by averaging, such as the signal shown in FIG. 3. As used herein, a "non-leaking voxel" means a voxel for which any leakage is at too low a level to be detected in the images. Distinguishing leaking voxels and non-leaking voxels is optionally done by looking at the uncorrected signal, for example $\Delta R_2^*(t)$ in the case of DSC-MRI imaging, at relatively late times, for example 60 or 70 or 80 seconds after the contrast agent is first introduced into the bloodstream. These "relatively late times" are times by which the contrast agent concentration in the arteries, and in the capillaries, is expected to be much smaller than its peak value. But for voxels with substantial leakage, a substantial concentration of contrast agent will remain in the EES. A level of signal corresponding to zero contrast agent concentration is optionally determined from the signal at relatively early times, before any contrast agent has reached the brain, as indicated by the initial rise time in the signal. For example, in the plots of $\Delta R_2^*(t)$ shown in FIGS. 2, 3A, 3B, and 4, this initial rise time is about 25 seconds after the contrast agent was introduced into the bloodstream, and "early times" would mean less than 25 seconds after the contrast agent was first introduced into the bloodstream. Optionally, the signal at early times, and/or the signal at late times, is averaged over a range of times, for example over 10 or 20 or 30 seconds, to reduce noise. This averaging comprises finding a mean value, a median value, or any other type of averaging that can be used to reduce noise; the inventors have found that using the median value works well. Alternatively, the signal at early times, and/or the signal at late times, is based only on a single early time or a single late time. As used herein, "times" or "a range of times" or "a time range" can refer to a single time or to an extended time interval.

A range of possible values of the signal at late times, expected for non-leaking voxels but not for substantially leaking voxels, is identified, and voxels are identified as non-leaking voxels if the signal at late times falls within that expected range. For example, non-leaking voxels are optionally identified as any voxels for which the signal at late times is much closer to the signal at early times, for example closer by at least a factor of 10 or 20 or 30, than the signal at early or late times is to the peak signal, when contrast agent has reached its peak concentration in the capillaries of the brain. A different range of possible values of the signal at late times, expected for substantially leaking voxels but not for non-leaking voxels, is also identified, and voxels are considered to be substantially leaking if their signal at late times is within that range. For example, substantially leaking voxels are optionally identified as voxels for which the signal at late times differs from the signal at early times by a substantial fraction of the difference between the signal at early times and the peak signal, for example more than 5% or more than 10% of the difference between the signal at early times and the peak signal.

Alternatively, if DSC-MRI imaging is used, a substantially leaking voxel is identified as any voxel for which the signal $\Delta R_2^*(t)$ at late times is negative. A non-leaking voxel is optionally identified, in this case, as any voxel for which the signal at late times is positive. These definitions are generally useful for DSC-MRI imaging, though not for CT imaging, because in DSC-MRI imaging contrast agent in the EES generally has the opposite effect on MRI signal amplitude, due to $T_1$ effects, than contrast agent in the capillaries. Optionally, some voxels that have marginal behavior at late times are not classified either as non-leaking voxels or as substantially leaking voxels. Their signals need not be corrected for leakage, because any leakage they undergo is relatively small, but they are not counted as non-leaking voxels for purposes of finding the signal averaged over voxels that do not exhibit leakage, because they may have a small amount of leakage.

Optionally, other criteria are used to identify substantially leaking voxels, or non-leaking voxels, in addition to or instead of using the range of the signal $\Delta R_2^*(t)$ as described above. For example, within the brain, typically only voxels in certain types of tumors have significant leakage, and optionally only voxels that are known to be located in such tumors, based on other criteria, are considered as possible candidates for leaking voxels, or all such voxels are considered to be leaking voxels for the purposes of the method of flowchart 100. Similarly, all brain tissue voxels not located in brain tumors, or not located near brain tumors, are optionally identified as non-leaking voxels even without looking at their $\Delta R_2^*(t)$ at late times. Even if a small number of such voxels turn out to exhibit leakage, this may have very little effect on the average $\Delta R_2^*(t)$ calculated for non-leaking voxels. Alternatively, voxels are identified as non-leaking voxels only if they are not located in or near brain tumors, and they have $\Delta R_2^*(t)$ at late times in the expected range for non-leaking voxels.

At 110, the measured signals $\Delta R_2^*(t)$ from one or more of the identified leaking voxels, not yet corrected for leakage, are found.

Figure 2:
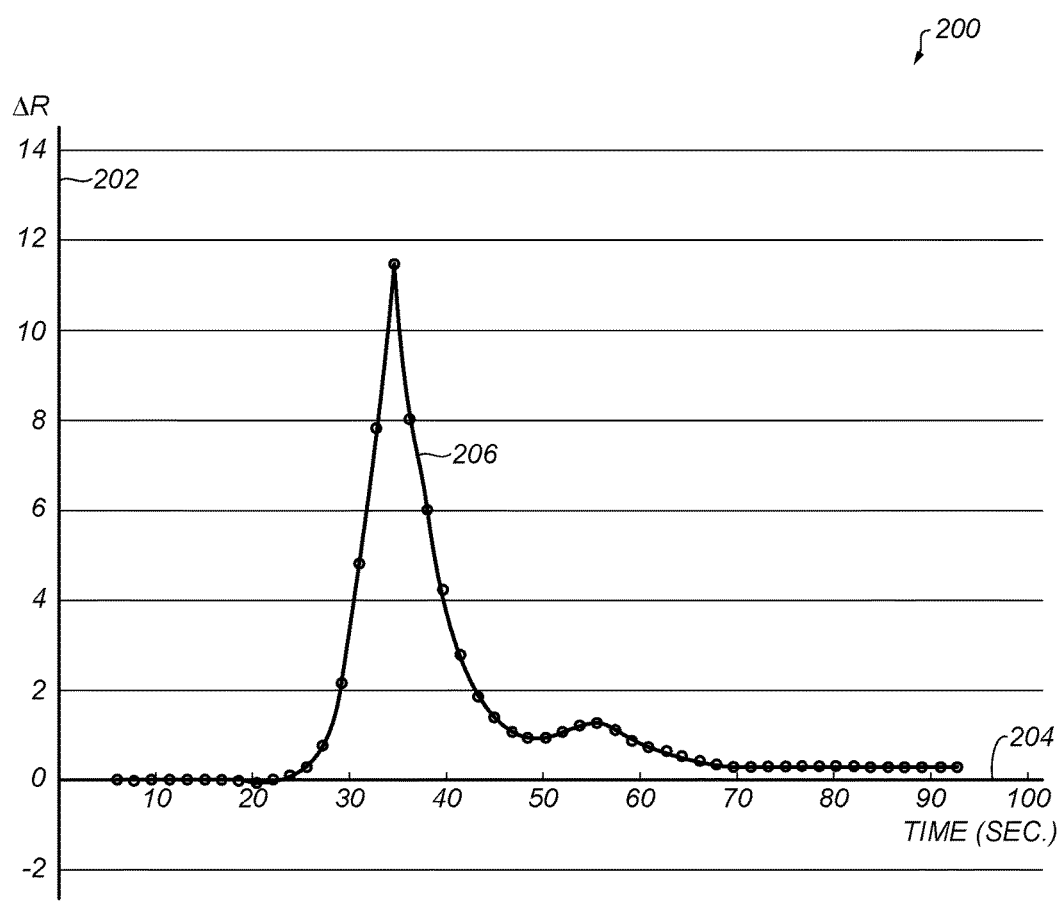
FIG. 2 is a plot of an average value of $\Delta R_2^*$ as a function of time for non-leaking voxels, for an exemplary series of DSC-MRI images of the brain of an exemplary subject with a brain tumor that has some leaking voxels.

At 112, an average of the measured $\Delta R_2^*$ for the identified non-leaking tissue voxels is found, as a function of time t over the time period when the images were acquired. Optionally, this average is found for all the identified non-leaking tissue voxels in the image. Alternatively, some non-leaking tissue voxels, which are identified by some means as possibly being abnormal, are excluded from the average, and only voxels believed to be healthy tissue are used. An example of a curve for this average $\Delta R_2^*(t)$ for non-leaking voxels, in a subject with a brain tumor, is shown in FIG. 2, in plot 200. A vertical axis 202 gives the values of $\Delta R_2^*$ in arbitrary units. A horizontal axis 204 gives the time t in seconds. Curve 206 is the curve for the average $\Delta R_2^*(t)$ for non-leaking voxels. The concentration of contrast agent starts to rise at about t=25, reaches a peak at about t=35, and has fallen almost back to zero at t=50. A further small bump centered at t=55 is due to the second pass of the contrast agent through the subject's circulatory system. At later times, t=65 to 90, the contrast agent has largely spread out throughout the circulatory system, and the concentration of contrast agent remains at a very low value, about 3% of its peak value.

In some embodiments of the invention, instead of providing images and deriving the artery input function, the average signal $\Delta R_2^*(t)$ for non-leaking voxels, and the measured signal $\Delta R_2^*(t)$ for one or more leaking voxels from the images, the artery input function and these signals are provided directly, and the method begins at this point, at 114. For example, the method could be used to re-analyze $\Delta R_2^*(t)$ signals that had been derived from images some time earlier, in order to obtain an improved correction for leakage.

At 114 in FIG. 1, the measured $\Delta R_2^*(t)$ curves for leaking voxels are optionally fitted to a model curve with at least one free parameter that depends on a leakage rate. For example, in an exemplary embodiment of the invention, a model is used that has two free parameters $K_1$, which depends on cerebral blood volume, and $K_2$, which depends on leakage rate. This model, which is based on a model used by Weisskoff et al, assumes that the concentration, in that voxel, of the contrast agent that is still in the capillaries has the same shape of $\Delta R_2^*(t)$ as the average $\overline{\Delta R^*_2(t)}$ for non-leaking voxels, for example curve 206 in FIG. 2, although it is multiplied by a constant factor $K_1$ to account for the fact that the voxel may have a different cerebral blood volume (volume fraction of blood vessels) than the average for the non-leaking voxels. The concentration in the voxel of contrast agent that has leaked into the EES is assumed to start out at zero, and to increase in time at a rate that is proportional to the concentration of contrast agent in the capillaries in that voxel. This assumption should be valid if the capillaries in the leaking voxel have a permeability to contrast agent that stays constant during the time the images are acquired, and if the concentration of contrast agent in the EES is low enough so that any backflow of contrast agent from the EES to the capillaries can be ignored. It is also assumed that the concentration of contrast agent in the EES is low enough so that its effect on $\Delta R_2^*$, due to its effect on $R_1$, is proportional to the concentration of contrast agent in the EES. As noted above, increased concentration of contrast agent in the EES makes a negative contribution to $\Delta R_2^*$, so the term in the model curve representing contrast agent in the EES is given a minus sign. The model curve that is fitted to the measured $\Delta R_2^*(t)$ in the leaking voxels is then $$K_1\overline{\Delta R^*_2(t)}-K_2\int_0^t \overline{\Delta R^*_2(\tau)}d\tau$$

where the free parameter $K_1$ is a measure of the cerebral blood volume of the voxel, and the free parameter $K_2$ is a measure of the permeability of the voxel to leakage of contrast agent.

Any known method of curve fitting can be used to find a best fit of the free parameters $K_1$ and $K_2$ to the measured $\Delta R_2^*(t)$ for the leaking voxel. For example, values of $K_1$ and $K_2$ are found that minimize the mean value of the square of the difference between the measured $\Delta R_2^*(t)$ and the fitted curve $K_1\overline{\Delta R^*_2(t)}-K_2\int_0^t \overline{\Delta R^*_2(\tau)}d\tau$, for all times t for which $\Delta R_2^*(t)$ was measured. Any known method may be used to find the values of $K_1$ and $K_2$ for which this mean value is minimized. It should be understood that the exact best fit values need not be found, but, for example, an iterative procedure may be used to zero in on the best fit values, and when the values are close enough to the best fit according to a convergence criterion, the procedure ends and those values for $K_1$ and $K_2$ are used.

Because the model function is a linear combination of two known functions oft, the linear coefficients $K_1$ and $K_2$ that minimize the mean square difference between the model function and the measured $\Delta R_2^*(t)$ can be found directly using the method of linear least squares, by solving two linear equations for the two unknowns $K_1$ and $K_2$. This method is described, for example, in the Wikipedia article on "Least Squares," found at <https://en.wikipedia.org/wiki/Least_squares>.

Alternatively, $K_1$ is set at a fixed value such that $K_1\overline{\Delta R^*_2(t)}$ matches the maximum value of $\Delta R_2^*(t)$ for this voxel, or matches the maximum rise rate for this voxel, and only $K_2$ is used as a free parameter, in fitting $\Delta R_2^*(t)$ to the model function. This procedure is expected to give a best fit value of $K_2$ similar to the value found treating both $K_1$ and $K_2$ as free parameters, because during the time when $\Delta R_2^*(t)$ is rising, and even when it is at its peak value, $\Delta R_2^*(t)$ is typically dominated by contrast agent in the capillaries, with contrast agent in the EES making an important contribution only later in time.

Alternatively, a model for the leakage is used which does not ignore backflow of contrast agent from the EES into the capillaries, such as the two-compartment model described by Bjornerud, cited above. In such a model, there is a third free parameter, the volume $v_e$ of the EES in each voxel, in addition to the blood volume parameter $K_1$ and the leakage rate parameter $K_2$. The model equation is no longer a linear function of the free parameters, and finding the best fit to $K_1$, $K_2$, and $v_e$ can be done, for example, by solving a nonlinear least squares problem iteratively, as described in the Wikipedia article on "Least Squares," or by any other method of nonlinear curve fitting.

Figure 3A:
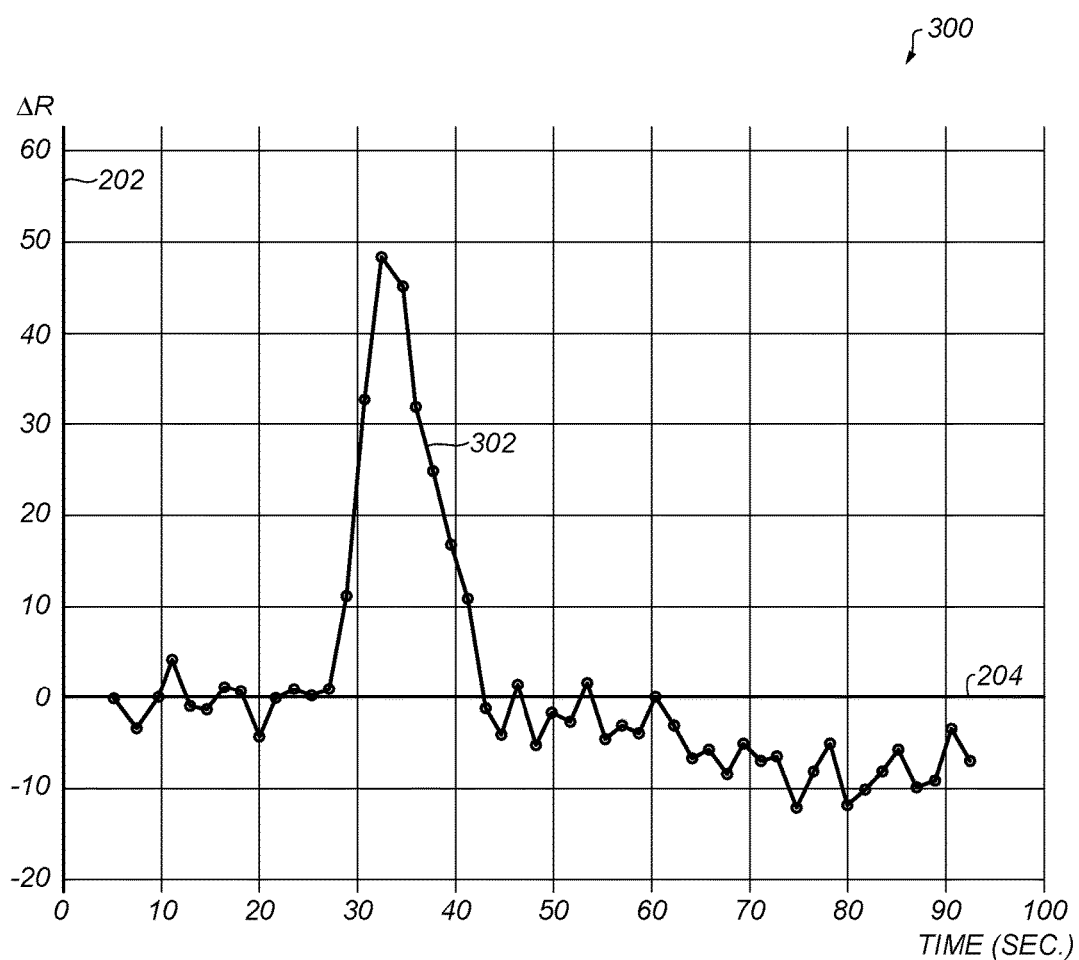
FIG. 3A is a plot of measured $\Delta R_2^*$ as a function of time, for an exemplary voxel exhibiting leakage in the brain of the subject for which the average $\Delta R_2^*$ as a function of time for non-leaking voxels is shown in FIG. 2.
Figure 3B:
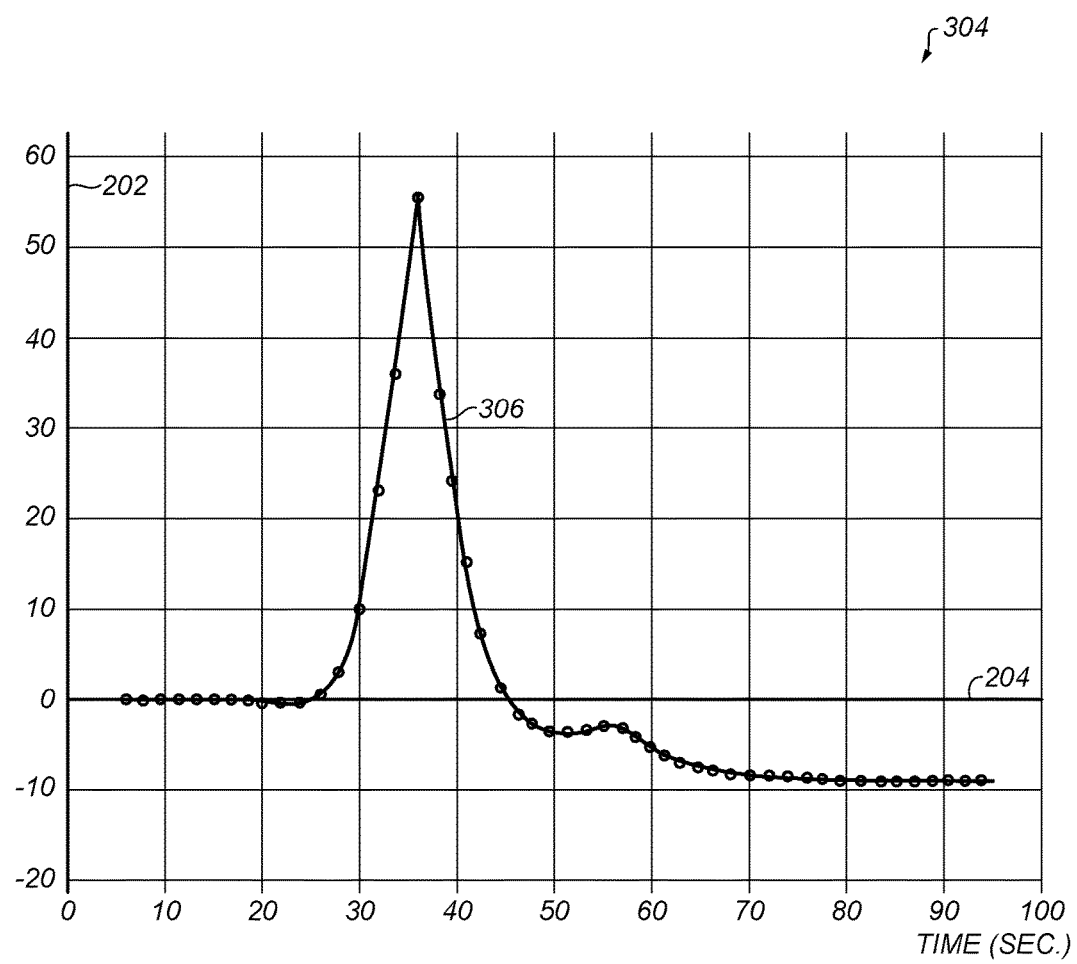
FIG. 3B is a plot of the best fit of the $\Delta R_2^*$ as a function of time shown in FIG. 3A, to $K_1$ times the average $\Delta R_2^*$ as a function of time for non-leaking voxels, plus $K_2$ times an integral over time of the average $\Delta R_2^*$ as a function of time for non-leaking voxels, for any pair of values of blood volume free parameter $K_1$ and leakage rate free parameter $K_2$.

FIG. 3A shows a plot 300 of the measured $\Delta R_2^*(t)$ for a leaking voxel in the subject's brain. Note that curve 302 falls below zero at t greater than about 45, indicating that there is significant leakage of contrast agent into the EES. FIG. 3B shows a plot 304 of a best fit of curve 302 in FIG. 3A to a model curve based on the average $\overline{\Delta R^*_2(t)}$ for non-leaking voxels shown in FIG. 2. The best fit, shown as curve 306 in FIG. 3B, has $K_1$=5.1092, and $K_2$=0.084758. Like the measured curve, the fitted curve is negative at t greater than about 45, due to the concentration of contrast agent remaining in the EES, after most of the contrast agent in the bloodstream has dissipated.

Referring again to flowchart 100 in FIG. 1, at 116 the best fit value of $K_2$ found at 114 is used to find a correction for leakage to the measured $\Delta R_2^*(t)$ for the leaking voxel. This is optionally done by first finding the difference between the best fit model function, and the model function with the free parameter depending on leakage set to a value corresponding to no leakage, keeping any other free parameters the same, and then subtracting that difference from the measured $\Delta R_2^*(t)$, to find the corrected $\Delta R_2^*(t)$. For example, if the model function is $K_1 \overline{\Delta R^*_2(t)} - K_2 \int_0^t \overline{\Delta R^*_2(\tau)} d\tau$, then we find the difference between this function, with $K_1$ and $K_2$ at their best fit values, and the model function with the leakage parameter $K_2$ set to zero, which is $K_1 \overline{\Delta R^*_2(t)}$. This difference is $-K_2 \int_0^t \overline{\Delta R^*_2(\tau)} d\tau$, which is subtracted from the measured $\Delta R_2^*(t)$ to find the corrected $\Delta R_2^*(t)$. The corrected signal $\Delta R_2^*(t)$ for the leaking voxel may then be expressed as:

$$\Delta R^*_{2corr}(t) = \Delta R^*_{2meas}(t) + K_2 \int_0^t \overline{\Delta R^*_2(\tau)} d\tau$$

Note that the $K_2$ term in the model function has a minus sign in front of it, to reflect the fact that it is normally negative in DSC-MRI imaging, so in the equation above, subtracting the $K_2$ term means adding a term with a plus sign in front of it. If the model function has a nonlinear dependence on the leakage parameter, for example if it is based on a model that includes backflow of contrast agent from the EES into the capillaries, then in general the correction to $\Delta R_2^*(t)$ will not be proportional to the leakage parameter $K_2$, but will have a more complicated dependence on the leakage parameter.

Figure 4:
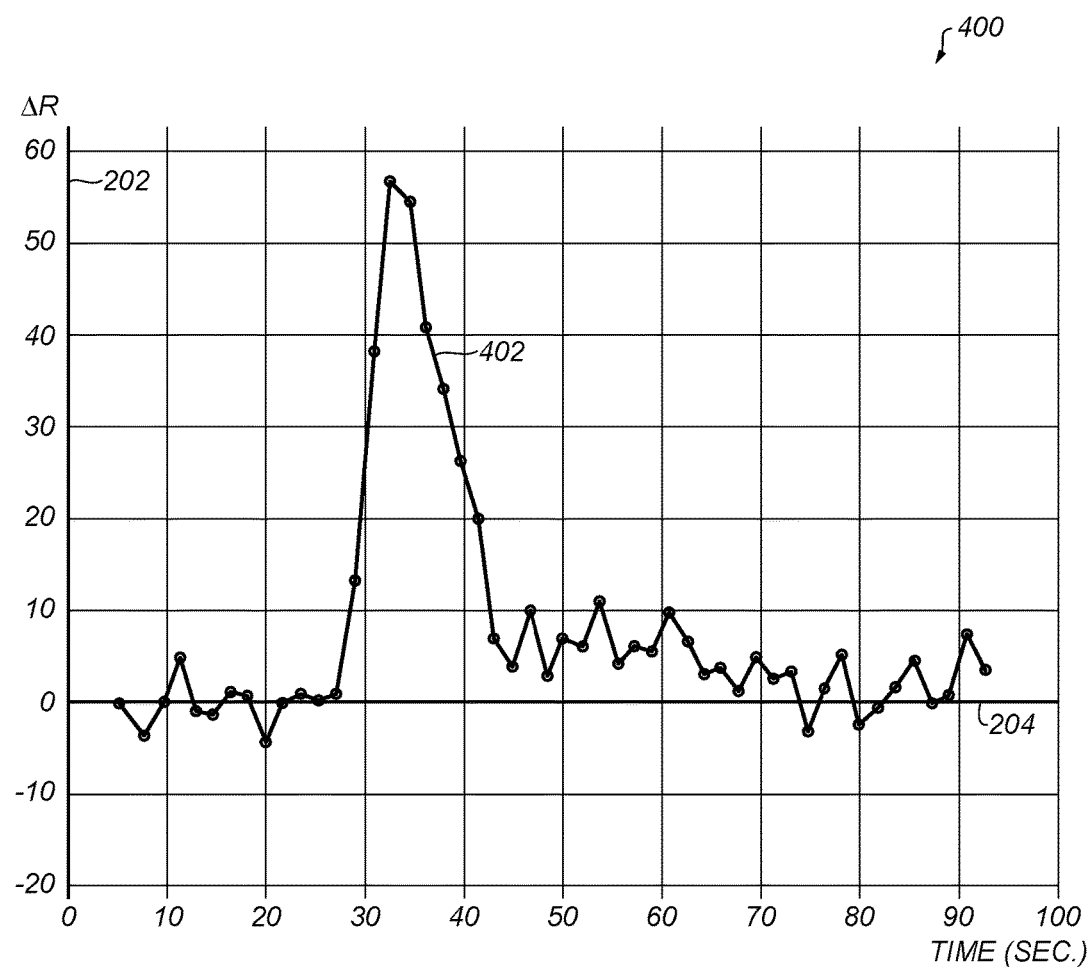
FIG. 4 is a plot of the measured $\Delta R_2^*$ as a function of time shown in FIG. 3A, corrected for leakage by removing the $K_2$ term for the best fit $K_2$ shown in FIG. 3B.

FIG. 4 shows a plot 400 of the corrected $\Delta R_2^*(t)$ for the leaking voxel whose measured $\Delta R_2^*(t)$ is shown in FIG. 3A. Corrected curve 402, with the contribution from the EES effectively removed, remains positive at large t, except for a few places where it dips slightly below zero due to noise.

At 118, the artery input function, found at 104, is deconvolved from the corrected signal $\Delta R_2^*(t)$ for the leaking voxels, to find a corrected residue function R(t) for the leaking voxels. It should be noted that this procedure is not done by Weisskoff et al, who use their corrected $\Delta R_2^*(t)$ for leaking voxels only to find the cerebral blood volume for those voxels. Finding the cerebral blood volume does not require finding the residue function, but can be done simply by integrating the corrected $\Delta R_2^*(t)$ over time. Deconvolving the artery input function from the corrected $\Delta R_2^*(t)$, and finding the residue function, also makes it possible to find hemodynamic parameters such as cerebral blood flow and mean transit time for the leaking voxels, corrected for leakage.

The concentration of contrast agent $C_t(t)$ in tissue (not including any contrast agent in the EES) is equal to the concentration of contrast agent in the arteries $C_a(t)$ convolved with the cerebral blood flow F times the residue function R(t). This relation may be expressed by the equation:

$$C_t(t) = C_a(t) \otimes FR(t)$$

This relation is still true if the tissue concentration $C_t$ and artery concentration $C_a$ are replaced respectively by the corrected signal $\Delta R_2^*(t)$ for the tissue voxel, and $\Delta R_2^*(t)$ for the arteries, since these quantities are respectively proportional to the concentrations of contrast agent in the tissue (not counting any contrast agent in the EES) and the arteries. To find the residue function, the artery input function $\Delta R_2^*(t)$ has to be deconvolved from the corrected $\Delta R_2^*(t)$ in the leaking voxel of the tissue.

One method of performing a deconvolution of two functions of time is to express the two functions as vectors, with each component of the vector being the function evaluated at one of a discrete set of times. The convolution relation between the functions is then expressed as a matrix equation relating the two vectors, and the matrix is inverted to solve the matrix equation for one of the vectors. For example, if a discrete function g is equal to the convolution of discrete functions f and h, then $$g[i] = \sum_{j=1}^{i} f[i-j+1] \cdot h[j]$$

This can be written in matrix form as g=Fh, where $F_{ij}$=f[i−j+1] for i≥j, and $F_{ij}$=0 for i<j, and g and h are vectors whose components are g[i] and h[i]. Then, to deconvolve f from g to find h, the matrix F can be inverted, yielding $h=F^{-1}g$. In our case, the elements of the vector g are the values of the corrected $\Delta R_2^*(t)$ at the discrete times $t_i$ when the images were acquired, and the elements $F_{ij}$ of the matrix are the artery input function at times $t_{i-j+1}$ for i≥j, and 0 for i<j. Multiplying the vector g by the inverted matrix $F^{-1}$ will give the vector h, whose elements are the cerebral blood flow times the residue function R(t) at the discrete times $t_i$. In practice, the matrix F is often ill-conditioned, and should be regularized before inverting it. Also, if it has any eigenvalues that are very small, a pseudo-inverse of F may be used instead of a true inverse.

In general, any method known in the art may be used for deconvolving the artery input function from the corrected signal $\Delta R_2^*(t)$ at 118. Other methods include the use of Fourier transforms, the use of Laplace transforms, Wiener deconvolution, described in the Wikipedia article on "Wiener deconvolution," <https://en.wikipedia.org/w/index.php?title=Wiener_deconvolution&oldid=700573288>, and Bayesian deconvolution, described by G. Larry Bretthorst, "Bayesian interpolation and deconvolution," <http://citeseerx.ist.psu.edu/viewdoc/summary?doi=10.1.1.46.3051>.

Figure 5:
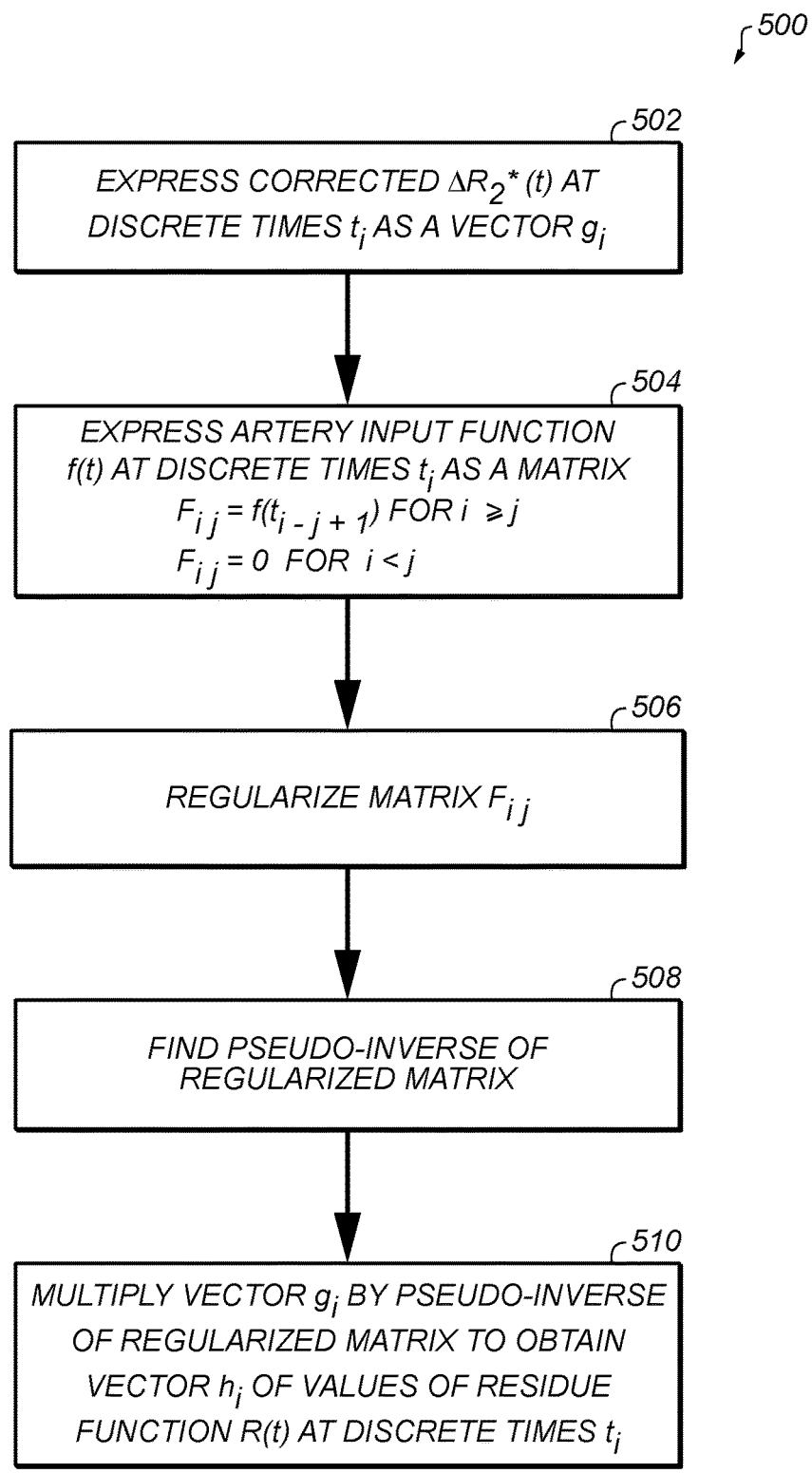
FIG. 5 is a flowchart showing details of an exemplary method of deconvolving a measured signal of contrast agent concentration, corrected for leakage, from the arterial input function, in order to find the residue function, according to the method of FIG. 1.

FIG. 5 shows a flowchart 500 for using the exemplary deconvolution method outlined above, involving the inversion (or pseudo-inversion) of a matrix F based on the artery input function. At 502, the corrected $\Delta R_2^*(t)$ for the leaking voxel, at discrete times $t_i$, is expressed as a vector with components $g_i$. At 504, the artery input function f(t), at discrete times $t_i$, is expressed as a matrix whose elements $F_{ij}$ are given by $f(t_{i-j+1})$ for i≥j, and 0 for i<j.

At 506, the matrix $F_{ij}$ is optionally regularized, by any known method of regularizing matrixes, if it is ill-conditioned. For example, some methods of regularizing matrixes are described in the Wikipedia articles on "Well-posed problem" <https://en.wikipedia.org/w/index.php?title=Well-posed_problem&oldid=690413559>, on "Condition number" <https://en.wikipedia.org/w/index.php?title=Condition_number&oldid=718497277>, and on "Tikhonov regularization" <https://en.wikipedia.org/w/index.php?title=Tikhonov_regularization&oldid=720904657>, as well as in P. C. Hansen, "The L-curve and its use in the numerical treatment of inverse problems," Computational Inverse Problems in Electrocardiology, number 5 in Advances in Computational Bioengineering, pages 119-142, WIT Press, Southampton, 2001; Thomas A. Bronikowski, Christopher A. Dawson, and John H. Linehan, "Model-free deconvolution techniques for estimating vascular transport functions," International Journal of Bio-Medical Computing 14(5):411-429, 1983, ISSN0020-7101, doi: http://dx.doi.org/10.1016/0020-7101(83)90024-7; and G T Gobbel and J R Fike, "A deconvolution method for evaluating indicator-dilution curves," Physics in Medicine and Biology, 39(11): 1833, 1994.

At 508, the inverse or pseudo-inverse of the regularized matrix is found, using any known method, for example singular value decomposition (SVD). See, for example, the Wikipedia article on Moore-Penrose pseudo-inverse <https://en.wikipedia.org/w/index.php?title=Moore%E2%80%93Penrose_pseudoinverse&oldid=719834705>.

At 510, the vector g is multiplied by the inverse or pseudo-inverse of the regularized matrix to obtain the vector h, whose values are the cerebral blood flow times the residue function R(t) at discrete times $t_i$. The residue function is generally defined as having a maximum value of 1, so the component of h with the largest value is the cerebral blood flow, and the other components of h may be divided by that component to obtain the normalized R(t). In some embodiments of the invention, the residue function is not normalized to have a maximum value of 1, but the un-normalized residue function is used to find hemodynamic parameters. The un-normalized residue function is sometimes referred to in the literature as the impulse response function. As used herein, "finding a residue function" and similar phrases mean finding an un-normalized residue function, a normalized residue function, or both.

Figure 6A:
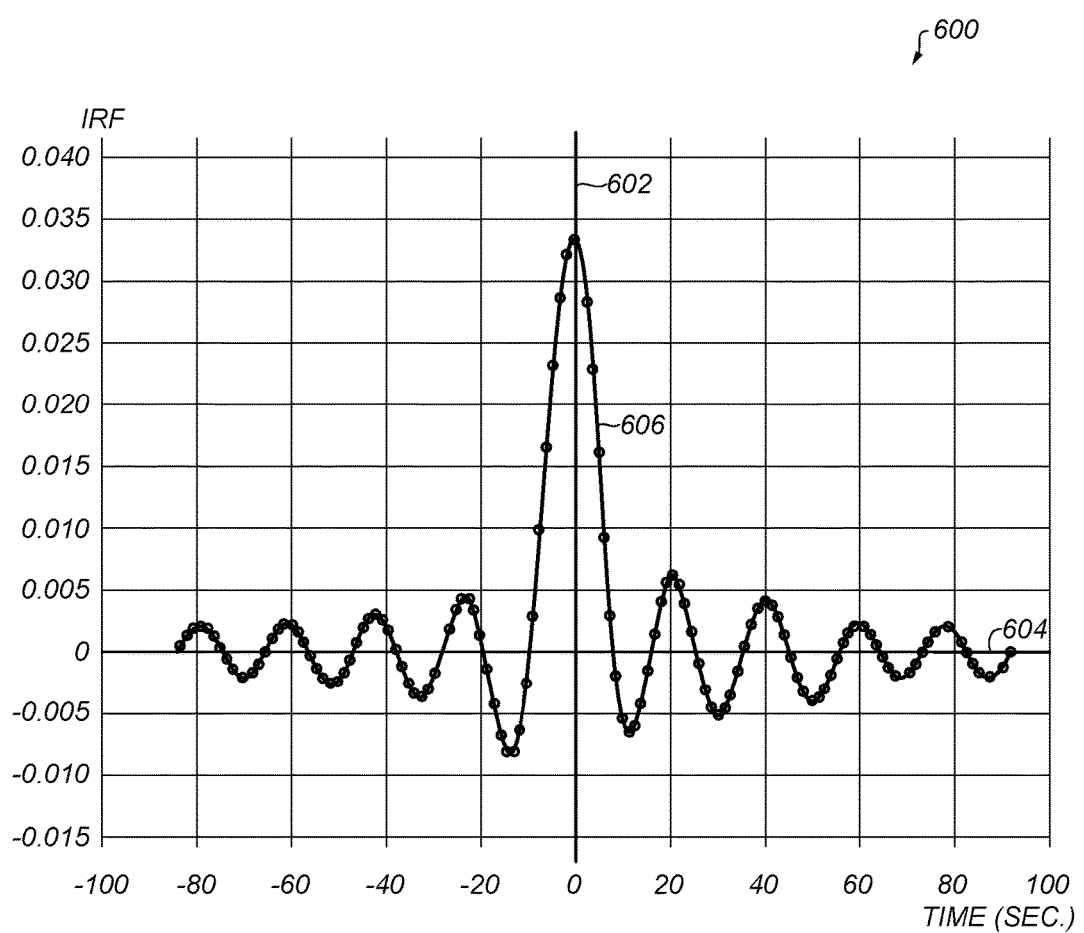
FIG. 6A is a plot of a residue function R(t) found from the corrected $\Delta R_2^*$ for the leaking voxel shown in FIG. 4, using the deconvolution method of FIG. 5.

FIG. 6A shows a plot 600 of the residue function R(t) obtained by deconvolving the artery input function found for the brain of the subject whose data is given in FIGS. 2, 3A, 3B, and 4, from the corrected $\Delta R_2^*(t)$ for the leaking voxel plotted in FIG. 4. However, vertical axis 602 has an arbitrary scale, and R(t) in this plot has not been normalized so that its maximum value is 1. Horizontal axis 604 shows the time in seconds. It should be understood that, in reality, R(t) is equal to 0 for t≤0, generally rises rapidly to its maximum value for t just slightly above 0, at least for healthy brain tissue, and then falls, roughly exponentially, with a characteristic time equal to the mean transit time (MTT). For some brain tissue, for example downstream from an ischemic stroke, R(t) may rise more slowly to its maximum value which may occur at an appreciable fraction of the MTT, and the MTT may be longer than for healthy brain tissue. In plot 600, the wiggles in curve 606 at early and late times are artifacts of the numerical method used to perform the deconvolution. However, the narrow central peak in curve 606 correctly reflects the sharp rise of R(t), with its peak value occurring at a time TMAX that is short compared to MTT, and correctly reflects the relatively small value of MTT, less than 10 seconds, found in healthy brain tissue. And the maximum height of curve 606 can be used (once the units in the vertical axis have been properly normalized) to accurately find the value of the cerebral blood flow. So it appears that this leaking voxel has normal perfusion properties.

Figure 6B:
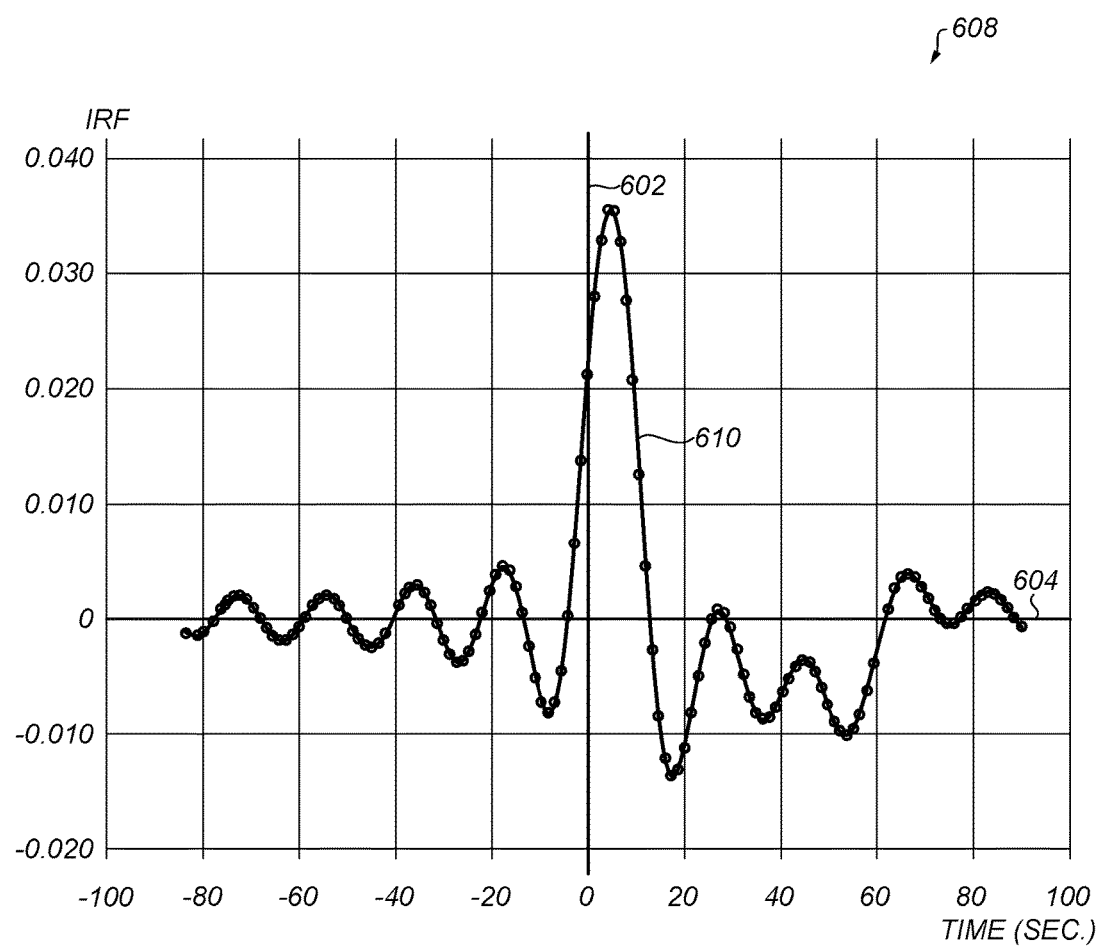
FIG. 6B is a plot of a residue function R(t) found from the uncorrected $\Delta R_2^*$ for the leaking voxel shown in FIG. 3A, using the deconvolution method of FIG. 5.

FIG. 6B shows a plot 608 of the residue function 610 that would be found if the uncorrected signal $\Delta R_2^*(t)$ shown in FIG. 3A were used, instead of the corrected signal shown in FIG. 4. The uncorrected residue function shows a value of TMAX, where R(t) has its maximum value, of about 3 seconds, which in a non-leaking voxel would indicate a significant abnormality in perfusion. It also has an unphysical dip into negative values. A comparison of FIGS. 6A and 6B shows that the signal with the leakage correction provides a more accurate residue function, and more accurate values for the hemodynamic parameters, than the uncorrected signal.

Figure 7:
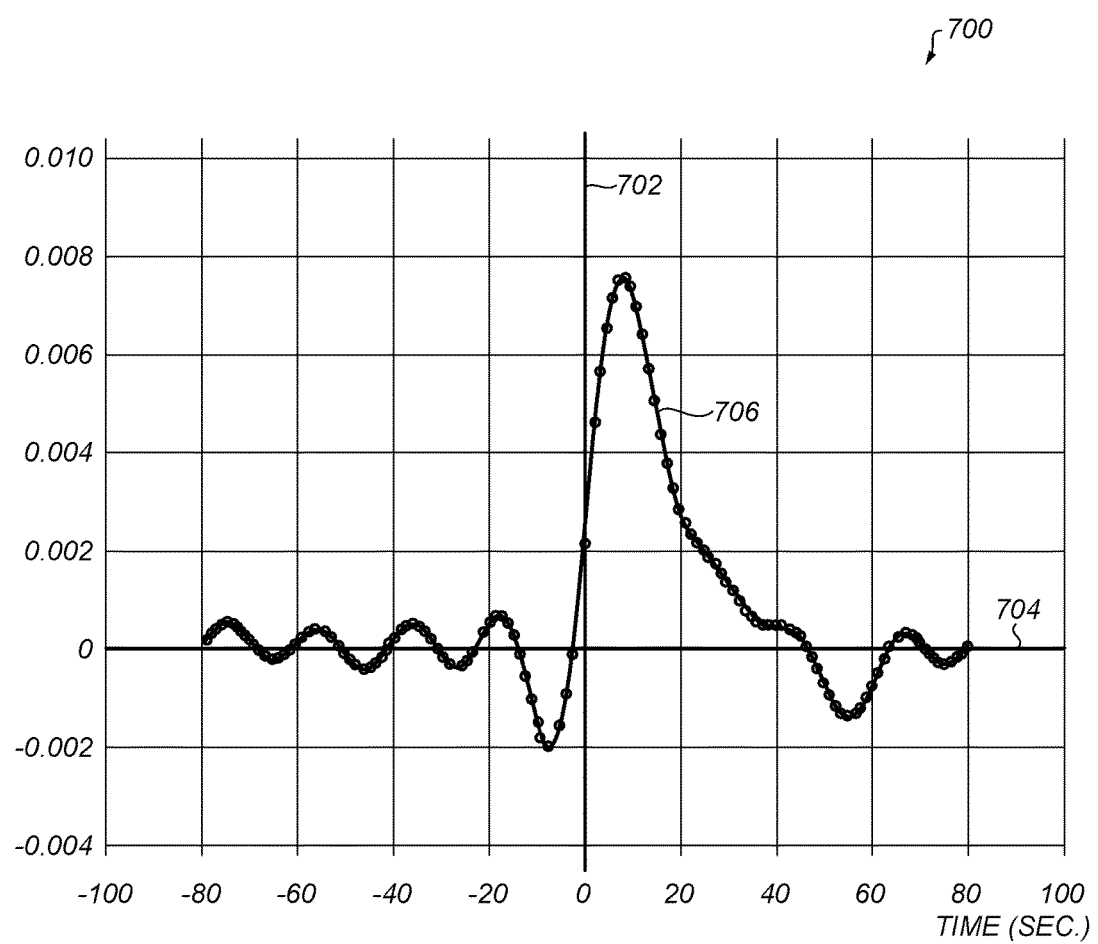
FIG. 7 is a plot of a residue function R(t) for an exemplary voxel in a brain image of a different subject, with abnormally long mean transit time.

Other voxels, whether leaking or non-leaking, may have abnormal R(t), with longer TMAX and longer MTT than is typical of healthy brain tissue. For example, FIG. 7 shows a plot 700 of R(t) for a different subject, with an ischemic stroke. Vertical axis 702 has an arbitrary scale, and horizontal axis 704 shows time in seconds. Again, the wiggles in curve 706 at early and late times are artifacts of the numerical methods used. But in contrast to curve 606, curve 706 has a broader central peak, indicating a larger MTT, and its peak is at a larger TMAX, both characteristic of brain tissue that has been affected by an ischemic stroke.

Optionally, once the corrected residue function R(t) has been found at 118 of flowchart 100, hemodynamic parameters are found for the leaking voxels, from the corrected R(t). The mean transit time, MTT, is found by integrating R(t) over time, where R(t) has been normalized so that its maximum value is 1. The cerebral blood flow (CBF), as noted above, is the value of the maximum component of the vector h, found at 510 in flowchart 500, and the cerebral blood volume (CBV) is MTT times CBF. The cerebral blood volume (CBV) can also be found by taking the integral of the corrected $\Delta R_2^*(t)$ over time, and dividing by the integral of $\Delta R_2^*(t)$ for the artery input function over time, even without finding R(t) and CBF. But finding CBV from R(t) and CBF has the potential advantage that the calculated CBV, CBF, and MTT will all be consistent with each other, even if the form of R(t) is distorted by artifacts due to the numerical methods used to perform the deconvolution. TMAX, the time at which R(t) is at its maximum, is also useful as a hemodynamic parameter. The time to peak, TTP, is the time at which $\Delta R_2^*(t)$ reaches its peak value, and this also does not require finding R(t). Finally, the permeability of the blood-brain barrier, characterized by the parameter $K_2$ found at 114, can also be found for all leaking voxels.

The artery input function found at 104 is also optionally deconvolved from the measured $\Delta R_2^*(t)$ for non-leaking voxels, in order to find the residue function R(t) for those voxels. The hemodynamic parameters are optionally found for the non-leaking voxels, including any of the hemodynamic parameters discussed above for the leaking voxels. Thus, the hemodynamic parameters can be found for all voxels, whether or not they are leaking, and can be meaningfully compared for leaking and non-leaking voxels.

Figure 8:
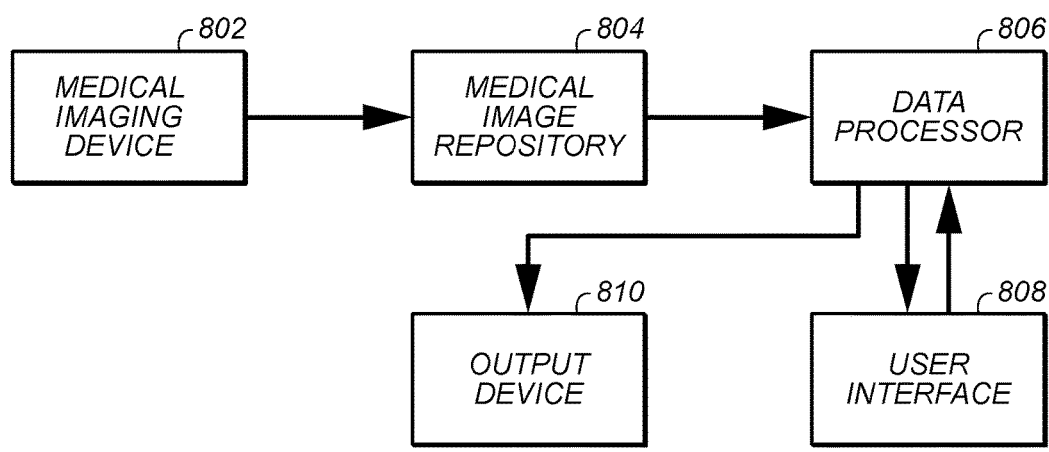
FIG. 8 is a schematic block diagram of a computer system for acquiring medical images of the brain and using them to perform the method of FIG. 1, according to an exemplary embodiment of the invention.

FIG. 8 shows a system 800 for acquiring medical images of a subject, and processing the medical images according to the method of flowchart 100, to obtain information on hemodynamic parameters of the subject. A medical imaging device 802, for example an MRI or CT device, acquires a series of medical images of the subject, for example images of the subject's brain, at different times after introducing contrast agent into the patient's bloodstream. The medical imaging device need not be connected to the other elements of system 800 at the time the images are processed, which might be much later. The images are sent by a communications link for storage in a medical image repository 804. A data processor 806, such as a personal computer or workstation, requests and obtains the images from repository 804, via a two-way communications link, and then processes the images according to the method of flowchart 100 in FIG. 1. Alternatively, the images are sent by medical imaging device 802 directly to data processor 806, for processing, for example in real time. Alternatively, the artery input function, the curves for one or more leaking voxels, and the average curve for non-leaking voxels, found at 104, 110, and 112 of flowchart 100, are stored after they are found in repository 804 together with the images, or instead of the images, and this data is retrieved, possibly much later, by data processor 806, in order to calculate the correction to the curves for the leaking voxels. In this case, data processor 806 need not have access to the images at all. A user interface 808, connected to data processor 806, controls the implementation of the data processing by data processor 806, for example controlling which images are processed, when they are processed, the values of control parameters used for the data processing, and where and how the results are displayed. User interface 808 includes, for example, a monitor, a keyboard, and a mouse, or any other user interface elements known in the art. An output device 810, for example a display monitor and/or a printer, displays the output of method 100, which can include a map showing the location of voxels in the brain with abnormal hemodynamic parameters including leakage, and an indication of the values of the hemodynamic parameters. It should be understood that data processor 806 in FIG. 8 may represent a plurality of different devices, with different devices possibly performing different elements of method 100. As used herein, "a data processor," "the data processor," and similar terms, may include such a plurality of devices.

The method of flowchart 100 improves the performance of data processor 806, and the performance of system 800 as a whole, because the method makes it possible for data processor 806 to find more accurate values of the residue function R(t), and of hemodynamic parameters derived from it, from brain images of patients, than was possible using prior art methods, at least under some circumstances. These improvements in function may make it possible to better diagnose and treat patients suffering from brain tumors and other pathologies.

It is expected that during the life of a patent maturing from this application many relevant medical imaging modalities will be developed and the scope of the term medical image is intended to include all such new technologies a priori. In general, different medical imaging modalities will require different types of contrast agents, and different ways of deriving the contrast agent concentration from the signal.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of determining a residue function for perfusion at one or more locations in a subject's brain tissue, from a series of medical images of the tissue acquired using a medical imaging modality at successive times after introducing a contrast agent into the subject's blood stream, the method correcting for a leakage of the contrast agent out of the blood stream into extravascular extracellular space (EES) of the tissue, the method comprising:

a) providing to a data processor a signal indicating contrast agent concentration as a function of time for one or more voxels of the tissue that exhibit the leakage at a significant level, a signal indicating an average or typical contrast agent concentration as a function of time for non-leaking voxels of the tissue, and an artery input function indicating a concentration of the contrast agent as a function of time in the arteries feeding into the tissue, the signals and artery input function being derived from the images;

b) fitting the signal for the voxels exhibiting leakage to an expected value for the signal as a function of time, using the data processor, according to a model with free parameters including at least a parameter depending on leakage rate, the model assuming that the concentration of contrast agent in the blood perfusing through a voxel has a same shape as a function of time as the average or typical contrast agent concentration for the non-leaking voxels;

c) using the model and best fit leakage rate parameter to find and make an expected correction for leakage, to the signal for contrast agent concentration as a function of time, for the voxels exhibiting leakage, using the data processor; and d) deconvolving the corrected signal for the voxels exhibiting leakage from the artery input function, to find the residue function for those voxels, using the data processor.

2. The method according to claim 1, wherein the imaging modality comprises computerized tomography (CT).

3. The method according to claim 1, wherein the imaging modality comprises magnetic resonance imaging (MRI), and the contrast agent comprises a paramagnetic contrast agent.

4. The method according to claim 3, wherein the MRI comprises dynamic susceptibility contrast (DSC) MRI.

5. The method according to claim 1, wherein providing the arterial input function comprises:

a) segmenting artery voxels in the medical images;
b) determining a concentration of the contrast agent in at least a portion of the artery voxels as a function of time; and
c) setting the arterial input function at the time when each of the medical images was acquired to a value based on a distribution of the concentration of contrast agent determined for the artery voxels in that medical image.

6. The method according to claim 1, wherein deconvolving the corrected signal comprises finding an inverse or pseudo-inverse of a matrix whose elements have values based on values of the corrected signal at a plurality of different times.

7. The method according to claim 6, wherein finding the inverse or pseudo-inverse of the matrix comprises regularizing the matrix.

8. The method according to claim 1, wherein providing a signal indicating an average or typical contrast agent concentration as a function of time for non-leaking voxels of the tissue comprises:

a) identifying non-leaking voxels of the tissue in the images; and
b) deriving the signal for each image acquisition time from image intensities for the identified non-leaking voxels in the image acquired at that time.

9. The method according to claim 8, wherein identifying non-leaking voxels of the tissue comprises:

a) segmenting and excluding voxels of blood vessels in the images;
b) selecting a late time range, long enough after the contrast agent is introduced so that a concentration of contrast agent in non-leaking voxels averaged over the late time range is expected to be at least 10 times lower than a peak concentration in that voxel;
c) identifying a range of possible signal amplitudes in the images that are expected for non-leaking voxels, but not for significantly leaking voxels, averaged over the late time range; and
d) identifying voxels as non-leaking voxels if their signal amplitudes, averaged over the late time range, falls within the range expected for non-leaking voxels.

10. The method according to claim 1, wherein providing a signal indicating contrast agent concentration for one or more voxels of the tissue that exhibit the leakage at a significant level comprises:

a) identifying the one or more voxels that exhibit the leakage at a significant level; and
b) deriving the signal for each image acquisition time, for each of the one or more voxels, from an image intensity for that voxel in the image acquired at that time.

11. The method according to claim 10, wherein identifying voxels that exhibit leakage at a significant level comprises:

a) segmenting and excluding voxels of blood vessels in the images;
b) selecting a late time range, long enough after the contrast agent is introduced so that a concentration of contrast agent in non-leaking voxels averaged over the late time range is expected to be at least 10 times lower than a peak concentration in that voxel;
c) identifying a range of possible signal amplitudes in the images that are expected for voxels that exhibit leakage at a significant level, but not for non-leaking voxels, averaged over the late time range; and
d) identifying voxels as exhibiting leakage at a significant level if their signal amplitude, averaged over the late time range, falls within the range expected for voxels that exhibit leakage at a significant level.

12. The method according to claim 1, wherein the model assumes that in each voxel, a permeability of capillaries to contrast agent does not change substantially over the times when the medical images are acquired, and that during those times, a concentration of contrast agent in the EES of that voxel increases at a rate that is proportional to the permeability times a concentration of the contrast agent in the capillaries of that voxel, neglecting any flow of contrast agent from the EES back into the capillaries.

13. The method according to claim 1, wherein the model assumes that in each voxel, a permeability of capillaries to contrast agent does not change substantially over the times when the medical images are acquired, and that during those times, a concentration of contrast agent in the EES of that voxel increases at a rate that is proportional to the permeability times a concentration of the contrast agent in the capillaries of that voxel minus a concentration of the contrast agent in the EES of that voxel.

14. The method according to claim 1, also comprising using the residue functions for those voxels to find one or more hemodynamic parameters for those voxels.

15. The method according to claim 14, wherein the hemodynamic parameters comprise one or more of a cerebral blood volume (CBV), a cerebral blood flow (CBF), a mean transit time (MTT), and a time of maximum value of the residue function (TMAX).

16. The method according to claim 1, wherein the free parameters of the model also include one or more other parameters in addition to the parameter that depends on leakage rate.

17. The method according to claim 16, wherein the one or more other parameters comprise a parameter that depends on blood volume.

* * * * *

UNITED STATES PATENT AND TRADEMARK OFFICE
CERTIFICATE OF CORRECTION

PATENT NO. : 10,213,178 B2
APPLICATION NO. : 15/706798
DATED : February 26, 2019
INVENTOR(S) : Ohad Silbert Page 1 of 1

It is certified that error appears in the above-identified patent and that said Letters Patent is hereby corrected as shown below:

In the Specification

Column 13, Line 9    Replace "tin" with --t in--
Column 14, Line 16    Replace "oft," with --of t,--

Signed and Sealed this
Seventh Day of May, 2019

Andrei Iancu
*Director of the United States Patent and Trademark Office*